United States Patent
Shibasaki et al.

(10) Patent No.: US 10,697,920 B2
(45) Date of Patent: Jun. 30, 2020

(54) GAS SENSOR

(71) Applicant: Riken Keiki Co., Ltd., Tokyo (JP)

(72) Inventors: Yoshikazu Shibasaki, Kasukabe (JP); Hirotaka Obata, Kasukabe (JP)

(73) Assignee: RIKEN KEIKI CO., LTD., Tokyo (JP)

( * ) Notice: Subject to any disclaimer, the term of this patent is extended or adjusted under 35 U.S.C. 154(b) by 238 days.

(21) Appl. No.: 15/724,971

(22) Filed: Oct. 4, 2017

(65) Prior Publication Data

US 2018/0106745 A1 Apr. 19, 2018

(30) Foreign Application Priority Data

Oct. 13, 2016 (JP) .................................. 2016-201573

(51) Int. Cl.
*G01N 27/16* (2006.01)
*G01N 33/00* (2006.01)

(52) U.S. Cl.
CPC ......... *G01N 27/16* (2013.01); *G01N 33/0027* (2013.01)

(58) Field of Classification Search
CPC ........................... G01N 27/16; G01N 33/0027
See application file for complete search history.

(56) References Cited

U.S. PATENT DOCUMENTS

| | | | | | |
|---|---|---|---|---|---|
| 5,989,398 | A | * | 11/1999 | Young | G01N 25/30 204/408 |
| 6,090,314 | A | * | 7/2000 | Handa | H01C 7/027 252/511 |
| 2014/0028340 | A1 | * | 1/2014 | Graf | B81C 1/00333 324/756.01 |

FOREIGN PATENT DOCUMENTS

JP 2001099801 A 4/2001
WO WO-2010084916 A1 * 7/2010 ............. G01N 27/16

* cited by examiner

*Primary Examiner* — Matthew D Krcha
(74) *Attorney, Agent, or Firm* — Lucas & Mercanti, LLP

(57) ABSTRACT

Disclosed is a gas sensor having high detection sensitivity, capable of detecting a gas at a low concentration and achieving lower power consumption. In the gas sensor including a gas detection element disposed on a thin-film insulator layer, the gas detection element includes: a heater layer provided on the thin-film insulator layer; and a gas detection layer having a thin-film thermistor part and an electrode part in contact with the thin-film, thermistor part, the gas detection layer being provided on the heater layer so as to be electrically insulated from the heater layer. The gas sensor is configured to detect a temperature change due to contact of a gas with the gas detection element on the basis of a change in resistance value in the thin-film thermistor part. The thin-film thermistor part preferably comprises a composite metal oxide containing $Fe_2O_3$, $TiO_2$ and $MgO$.

4 Claims, 4 Drawing Sheets

GAS SENSOR

CROSS REFERENCE TO RELATED APPLICATION

This Application claims the benefit of Japanese Patent Application No. 2016-201573 filed Oct. 13, 2016, which is incorporated herein by reference.

TECHNICAL FIELD

The present invention relates to a gas sensor using a MEMS technique, and specifically, to a contact combustion type or heat conduction type gas sensor.

BACKGROUND ART

A contact combustion type gas sensor used for detecting a combustible gas is configured to include a gas detection element having a gas sensitive part (an oxidation catalyst layer) formed by sintering an oxidation catalyst and an alumina support on a platinum wire coil, for example; and a compensation element insensitive to the combustible gas. The contact combustion type gas sensor having such a configuration has advantages such as a property of being less affected by water vapor and high responsiveness to gas, but has disadvantages such as difficulty in size reduction and large power consumption.

In recent years, contact combustion type gas sensors using the MEMS technique have been developed (see Patent Literature 1, for example). It is expected that the use of the MEMS technique achieves size reduction and lower power consumption.

CITATION LIST

Patent Literature

Patent Literature 1: Japanese Patent Application Laid-Open No. 2001-099801

SUMMARY OF INVENTION

Technical Problem

In the contact combustion type gas sensor described in Patent Literature 1, a metal conductor such as Pt is used as a detection part. Such a metal conductor, however, cannot obtain sufficient sensitivity due to its small rate of change in resistance value with respect to a temperature change.

The present invention has been made in view of the foregoing circumstances and has as its object the provision of a contact combustion type or heat conduction type gas sensor having nigh detection sensitivity, capable of detecting a gas at a low concentration and achieving lower power consumption.

Solution to Problem

According to the present invention, there is provided a gas sensor including a gas detection element disposed on a thin-film insulator layer, the gas detection element including: a heater layer provided on the thin-film insulator layer; and a gas detection layer having a thin-film thermistor part and an electrode part in contact with the thin-film thermistor part, the gas detection layer being provided on the heater layer so as to be electrically insulated from the heater layer.

The gas sensor is configured to detect a temperature change due to contact of a gas with the gas detection element on the basis of a change in resistance value in the thin-film thermistor part.

In the gas sensor of the present invention, the gas detection element may include a catalyst layer provided on the thin-film thermistor part in the gas detection layer. Then, the gas sensor may detect a temperature change in combustion neat of the catalyst layer on the basis of a change in resistance value in the thin-film thermistor part.

In the gas sensor of the present invention, the thin-film thermistor part may preferably comprise a composite metal oxide containing $Fe_2O_3$, $TiO_2$ and $MgO$. In the composite metal oxide, a ratio of $TiO_2$ relative to $Fe_2O_3$ may preferably be 0.1 to 10 mol %, and a ratio of $MgO$ relative to $Fe_2O_3$ may preferably be 0.5 to 10 mol %.

The gas sensor of the present invention may preferably include a cavity portion and the thin-film insulator layer on which the gas detection element is disposed may preferably be provided on the cavity portion.

Moreover, the gas sensor of the present invention may preferably include a second cavity portion provided at a position spaced apart from the cavity portion related to the gas detection element, a second thin-film insulator layer provided on the second cavity portion, and a compensation element disposed on the second thin-film insulator layer.

Advantageous Effects of Invention

According to the gas sensor of the present invention, the thermistor is used as an element for detecting a temperature change in the gas detection element, specifically, a temperature change due to the combustion heat of the catalyst layer or a temperature change due to the heat conduction of a contact gas. The thermistor has a large rate of change in resistance value with respect to a temperature change. Thus, the gas sensor of the present invention can obtain high detection sensitivity and can detect the gas at a low concentration.

According to the configuration in which the gas detection element including the heater layer and the gas detection layer is disposed on the thin-film insulator layer provided on the cavity portion, the cavity portion makes a heat-insulated structure. Thus, loss due to heat conduction to the members other than the thermistor can be reduced, high detection sensitivity can be obtained, and lower power consumption can be achieved.

DESCRIPTION OF EMBODIMENTS

A contact combustion type gas sensor according to an embodiment of the present invention will be described below in detail.

A contact combustion type gas sensor of the present invention is configured in such a manner that a gas detection element is disposed (supported) on a thin-film insulator layer provided on a cavity portion. The contact combustion type gas sensor of the present invention may have a diaphragm structure in which a thin-film insulator layer is provided so as to cover the entire opening of a cavity portion formed in a substrate, a microbridge structure in which a thin-film insulator layer is bridge-supported over a cavity portion so as to cover at least part of the cavity portion formed in a substrate or a microbridge structure in which a thin-film insulator layer is provided on a surface of a substrate via a cavity portion. When a cavity portion is formed in a substrate, the cavity portion may be formed by a through hole extending in a thickness direction of the substrate, or may be formed by a recess provided in a surface of the substrate. The shape of the cavity portion is not limited to any particular shape.

The gas detection element includes: a heater layer provided on the thin-film insulator layer; a gas detection layer having a thin-film thermistor part and a thermistor electrode part in contact with the thin-film thermistor part, the gas detection layer being provided on the heater layer so as to be electrically insulated from the heater layer; and a catalyst layer provided on the thin-film thermistor part in the gas detection layer. A temperature change due to combustion heat of the catalyst layer is detected on the basis of a change in resistance value in the thin-film thermistor part.

The contact combustion type gas sensor of the present invention may be configured to include a compensation element (temperature compensation element). In the contact combustion type gas sensor having such a configuration, the compensation element is disposed on a thin-film insulator layer provided on a cavity portion provided at a position spaced apart from the cavity portion related to the gas detection element. The compensation element has the same configuration as the gas detection element except that no catalyst layer is included or a catalyst layer of a type different from that of the catalyst layer related to the gas detection element is provided.

Taking a contact combustion type gas sensor having a microbridge structure as an example, a contact combustion type gas sensor according to the present invention will be specifically described below.

Figure 1:
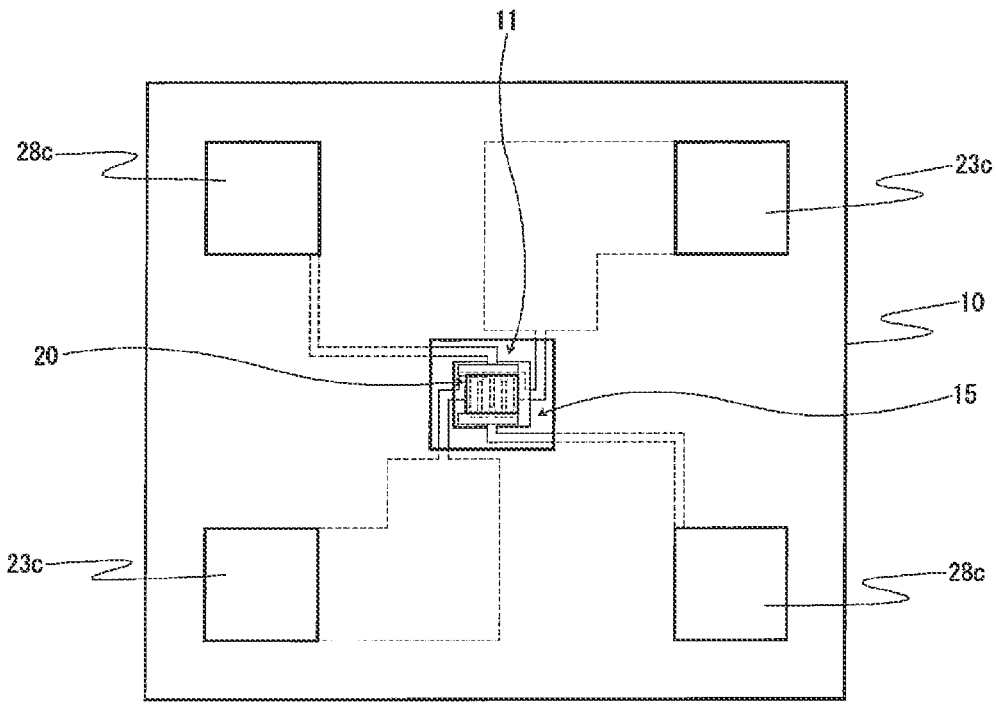
[FIG. 1] is a plan view schematically illustrating a configuration example of a contact combustion type gas sensor according to the present invention.
Figure 2:
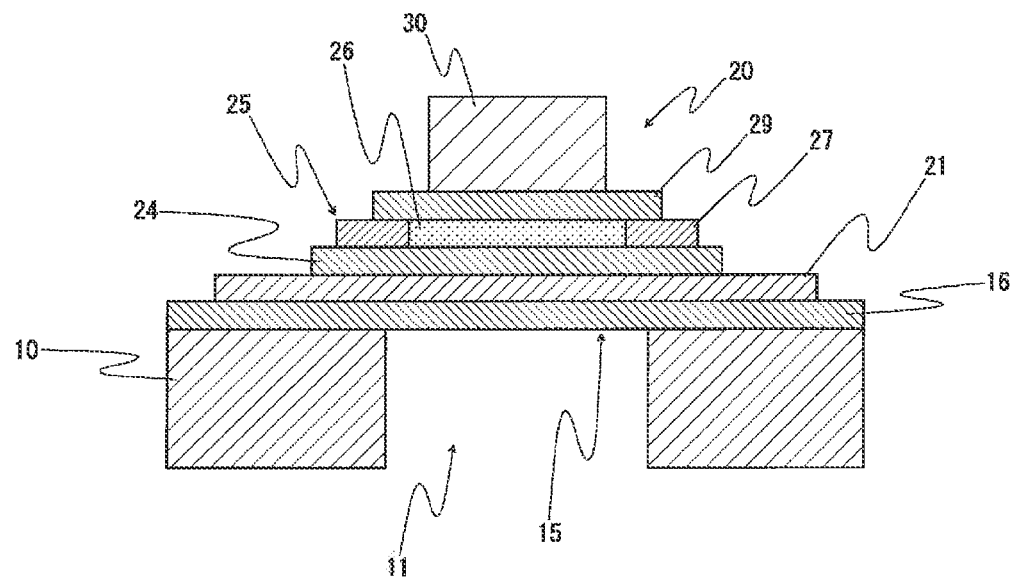
[FIG. 2] is a cross-sectional assembly diagram schematically illustrating a cross section of the contact combustion type gas sensor shown in FIG. 1, taken along the pattern of a thin-film heater.

FIG. 1 is a plan view schematically illustrating a configuration example of a contact combustion type gas sensor according to the present invention. FIG. 2 is a cross-sectional assembly diagram schematically illustrating a cross section of the contact combustion type gas sensor shown in FIG. 1, taken along the pattern of a thin-film heater.

The contact combustion type gas sensor in this example includes: a substrate 10 having a cavity portion 11 formed therein and made of silicon, for example; a thin-film insulator layer 15 bridge-supported over the cavity portion 11 so as to cover at least part of an opening of the cavity portion 11 in the substrate 10; and a gas detection element 20 supported on the thin-film insulator layer 15.

The substrate 10 is constituted by a semiconductor substrate such as a silicon substrate, for example.

The cavity portion 11 in the substrate 10 is formed by a through hole extending in a thickness direction of the substrate 10, for example. While only the cavity portion 11 for the gas detection element is provided in this example, two cavity portions 11 and 12, which form a pair including one used for the gas detection element and the other used for a compensation element, may be provided at positions spaced apart from each other (see FIG. 8).

Figure 3:
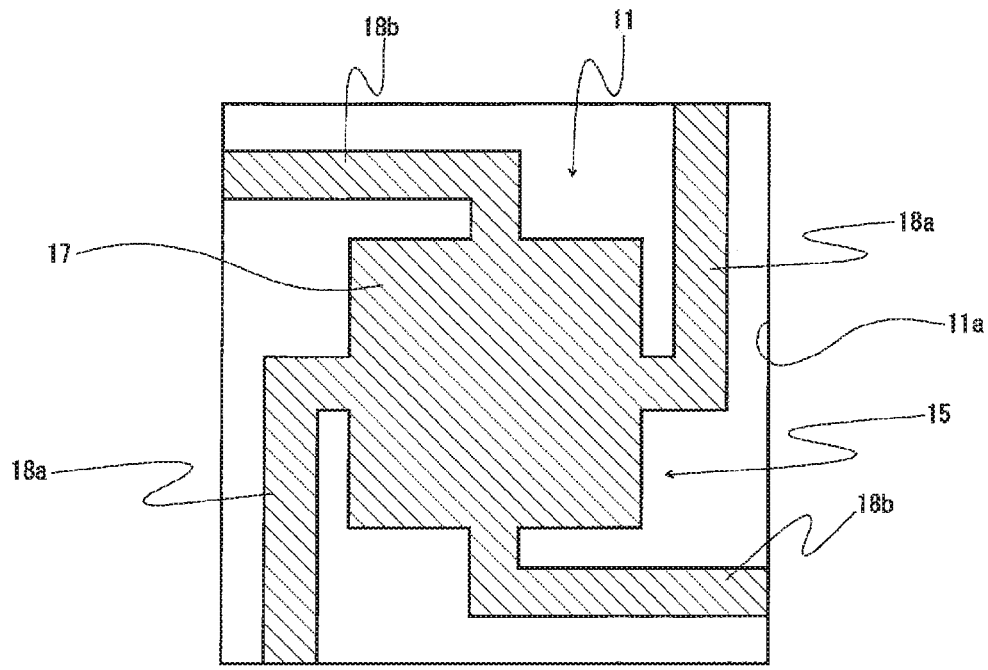
[FIG. 3] is a plan view illustrating a configuration of a thin-film insulator layer in the contact combustion type gas sensor shown in FIG. 1.

The thin-film insulator layer 15 is formed by removing part of a first insulating film 16 provided on a surface of the substrate 10. In the thin-film insulator layer 15, a base part 17 having a square shape in a planar view is bridge-supported by a plurality (two pairs, i.e., four in this example) of support beams 18a and 18b so that the base part 17 is positioned at the center of the opening as shown in FIG. 3. In FIG. 3, the reference numeral 11a denotes an opening edge of the cavity portion 11. Note that the thin-film insulator layer 15 is hatched in FIG. 3 for the purpose of illustration.

The first insulating film 16 (the thin-film insulator layer 15) is made by a multi-layer film comprising a first $SiO_2$ film, an $Si_3N_4$ film and a second $SiO_2$ film, for example, ($SiO_2/Si_3N_4/SiO_2$ multi-layer film). Such a construction can reduce distortion in the thin-film insulator layer 15 due to thermal stress.

The gas detection element 20 includes: a heater layer 21 provided on the thin-film insulator layer 15; a gas detection layer 25 having a thin-film thermistor part 26 and a thermistor electrode part 27 in contact with the thin-film thermistor part 26, the gas detection layer 25 being provided on the heater layer 21 via a second insulating film 24; and a catalyst layer 30 provided on the thin-film thermistor part 26 in the gas detection layer 25 via a third insulating film 29.

Figure 4:
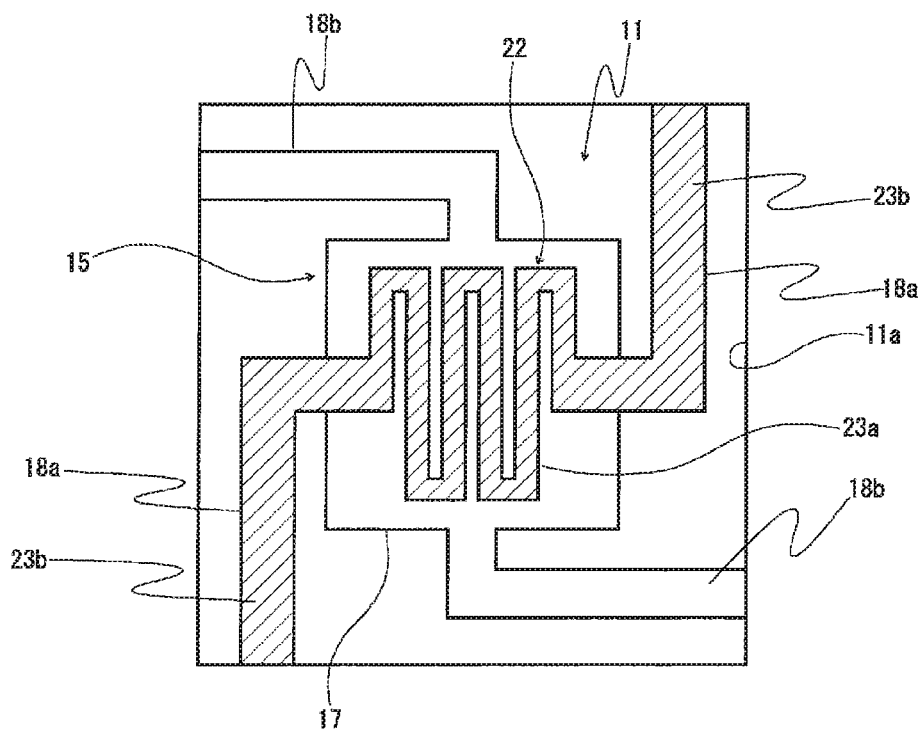
[FIG. 4] is a plan view illustrating a configuration of a heater layer in the contact combustion type gas sensor shown in FIG. 1.

The heater layer 21 is made by a thin-film heater 22 patterned on a surface of the first insulating film 16 and comprising a PtW film, for example. Specifically, the thin-film heater 22 includes: a heat generation part 23a formed in such a manner as to wind in a rectangular wave shape, for example; lead parts 23b continuous with both ends of the heat generation part 23a; and heater electrode parts 23c connected to the heat generation part 23a via the lead parts 23b as shown in FIG. 4. The heat generation part 23a is formed on the base part 17 of the thin-film insulator layer 15, and the lead parts 23b are formed on the pair of support beams 18a positioned opposed to each other. Note that the thin-film heater 22 is hatched in FIG. 4 for the purpose of illustration.

The heater layer 21 is formed on the first insulating film 16 preferably via a Cr film (not shown), for example, in order to improve adhesion with the first insulating film 16. Moreover, a Cr film (not shown), for example, is preferably formed on the heater layer 21 in order to improve adhesion with the second insulating film 24.

Figure 5:
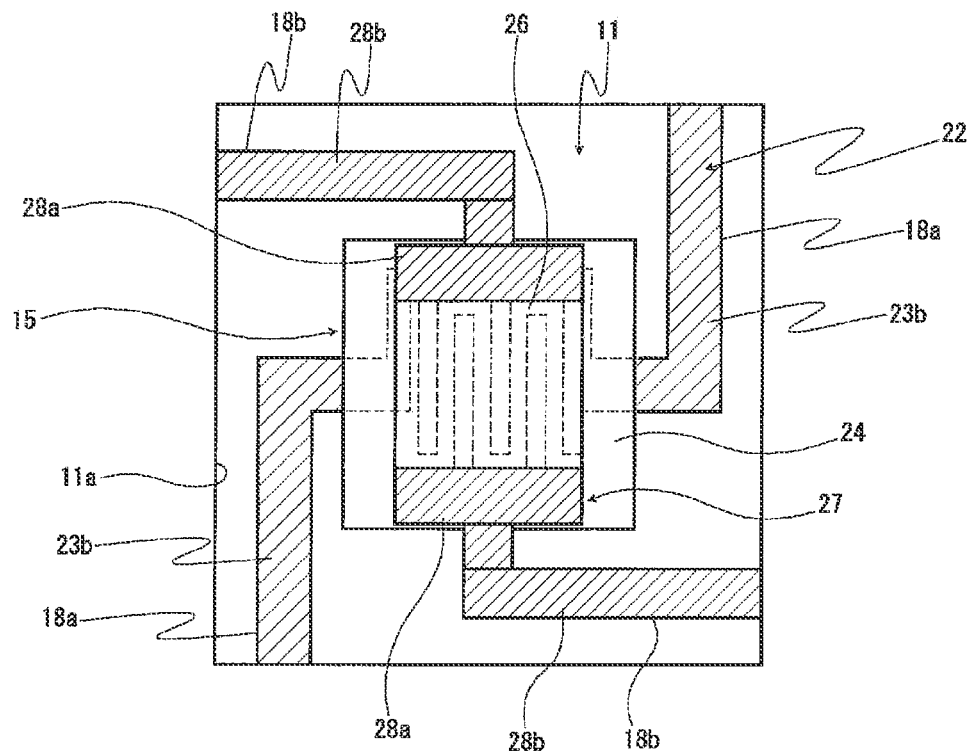
[FIG. 5] is a plan view illustrating a configuration of a gas detection layer in the contact combustion type gas sensor shown in FIG. 1.

The thermistor electrode part 27 constituting the gas detection layer 25 comprises a PtW film, for example. As shown in FIG. 5, the thermistor electrode part 27 includes: a pair of comb-shaped electrodes 28a patterned in such a manner that their comb teeth are arranged alternately at regular intervals; and terminal parts 28c connected to the pair of comb-shaped electrodes 28a via lead parts 28b. The pair of comb-shaped electrodes 28a is provided above the heat generation part 23a of the thin-film heater 22, and the lead parts 28b are provided on the pair of support beams 18b different from the support beams 18a on which the lead parts 23b of the thin-film heater 22 are provided in the thin-film insulator layer 15.

The thermistor electrode part 27 is provided on the second insulating film 24 preferably via a Cr film (not shown), for example, in order to improve adhesion with the second insulating film 24.

The thin-film thermistor part 26 constituting the gas detection layer 25 has a square shape in a planar view, for example, and is formed so as to cover the entire comb tooth portion in the pair of comb-shaped electrodes 28a, for example.

The thin-film thermistor part 26 is preferably made by a negative characteristic thermistor comprising a composite metal oxide containing $Fe_2O_3$, $TiO_2$ and $MgO$, for example, (an $Fe_2O_3$—$TiO_2$—$MgO$ composite metal oxide). Such a negative characteristic thermistor can stabilize the performance of the contact combustion type gas sensor by the inclusion of $MgO$.

In this negative characteristic thermistor, the ratio of $TiO_2$ relative to $Fe_2O_3$ is preferably 0.1 to 10 mol %, more preferably 0.5 to 7 mol %, and further preferably 0.5 to 5 mol %, for example. The ratio of $MgO$ relative to $Fe_2O_3$ is preferably 0.5 to 10 mol %, more preferably 1 to 8 mol %, for example.

Figure 6:
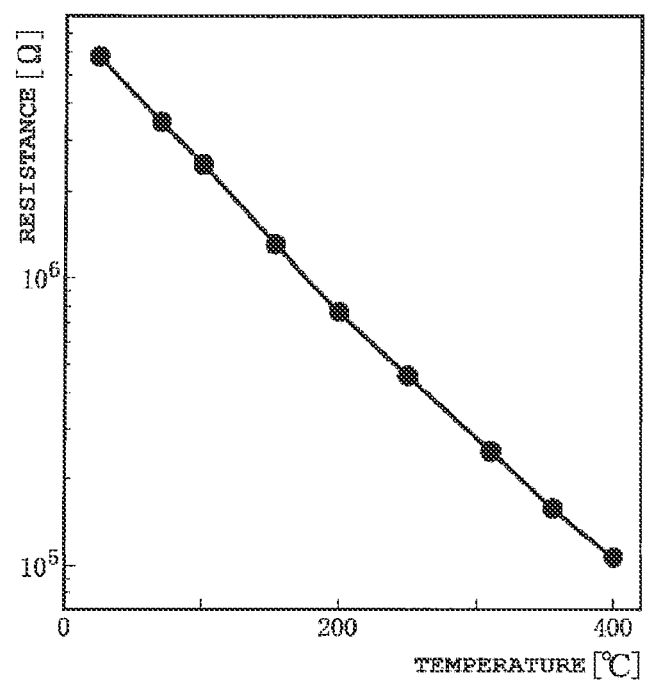
[FIG. 6] is a graph showing temperature-resistance characteristics of a thermistor material constituting a thin-film thermistor part in the contact combustion type gas sensor shown in FIG. 1.

FIG. 6 shows temperature-resistance characteristics in the negative characteristic thermistor comprising an $Fe_2O_3$—$TiO_2$—$MgO$ composite metal oxide wherein the ratio of $TiO_2$ relative to $Fe_2O_3$ is 5 mol % and the ratio of $MgO$ relative to $Fe_2O_3$ is 4 mol %. It has been confirmed from this graph that the rate of change in resistance value with respect to a temperature change in this negative characteristic thermistor corresponds to magnitude about five times as large as that of Pt, for example.

The catalyst layer 30 can be constituted by a material appropriately selected according to a type of a gas to be detected (combustible gas). In this example, the catalyst layer 30 comprises a $Pd/SnO_2$ catalyst or a $Pt/SnO_2$ catalyst obtained by subjecting a mixture of $SnO_2$ nanoparticles, a PVA solution and a Pd or Pt colloid solution to a thermal treatment (baking). Alternatively, the catalyst layer 30 may comprise a $Pd/ZrO_2$ catalyst or a $Pt/ZrO_2$ catalyst obtained by using $ZrO_2$ instead of $SnO_2$.

In the contact combustion type gas sensor described above, when current is applied to the heater layer 21 to heat the heater layer 21 to a predetermined temperature, the catalyst layer 30 is heated to a temperature suitable for an oxidation reaction with a combustible gas on a surface thereof. In this state, if the combustible gas comes into contact with the catalyst layer 30, the contact combustion of the combustible gas occurs on the surface of the catalyst layer 30, and thus the temperature of the catalyst layer 30 increases. Along with the temperature change in the catalyst layer 30, the temperature of the thin-film thermistor part 26 increases and the resistance value of the thin-film thermistor part 26 decreases in this example. On the basis of the change in resistance value of the thin-film thermistor part 26, the concentration of the combustible gas is detected.

According to the contact combustion type gas sensor having the above configuration, the gas detection element 20 including the heater layer 21 (heater part), the gas detection layer 25 (sensor part) and the catalyst layer 30 is basically disposed on the thin-film insulator layer 15 provided on the cavity portion 11 formed in the substrate 10 to form a heat-insulated structure. Moreover, the contact combustion type gas sensor is configured so that the heat capacity of the substrate 10 itself is reduced. Thus, loss due to heat conduction can be reduced, and lower power consumption can be achieved. Furthermore, a thermistor material constituting the thin-film thermistor part 26 used as an element for detecting a temperature change due to the combustion heat of the catalyst layer 30 has a large rate of change in resistance value with respect to a temperature change. Thus, high detection sensitivity can be obtained and the gas at a low concentration can be detected.

According to the contact combustion type gas sensor described above, in use applications not requiring very high detection sensitivity, a gas inflow to the contact combustion type gas sensor can be reduced to reduce degradation caused by the poisoning of the catalyst layer 30 by an S-containing gas such as an $H_2S$ gas or an Si-containing gas, for example. Thus, the life of the gas sensor can be expected to increase.

Furthermore, in the use applications not requiring very nigh detection sensitivity, an amount of the combustion catalyst can be reduced, and thus cost reduction and further reduction in power consumption due to operations at a lower temperature can be expected.

EXAMPLES

While specific examples of the present invention will now be described below, the present invention is not limited thereto.

Example 1

In accordance with the configurations shown in FIGS. 1 to 5, a contact combustion type gas sensor of the present invention was produced by the following method.

<Step of Forming First Insulating Film>

A p-type silicon wafer having a thickness of 500 μm and having a plane of crystal orientation <100> was used as a substrate. An $SiO_2$ film having a thickness of 4 μm was formed on a front surface of the substrate, and an $SiO_2$ film having a thickness of 1 μm was formed on a back surface of the substrate. Next, an $Si_3N_4$ film having a thickness of 2 μm was formed on the $SiO_2$ film on the front-surface side. An $SiO_2$ film having a thickness of 1 μm was further formed on the $Si_3N_4$ film. In this manner, a first insulating film was formed on the front surface of the substrate. The $SiO_2$ film and the $Si_3N_4$ film were formed by a sputtering technique.

<Step of Forming Microbridge Structure>

Patterning was performed on the $SiO_2$ film on the back-surface side by a photolithography technique, the $SiO_2$ film on the back-surface side was etched to open a window, and then the substrate was further etched to form a cavity portion.

Subsequently, patterning was performed on the first insulating film by the photolithography technique, and the first insulating film was etched to form a thin-film insulator layer having a microbridge structure in which a base part was bridge-supported by a plurality of support beams over the cavity portion formed in the substrate.

<Step of Forming Heater Layer>

After a Cr film having a thickness of 0.035 μm was formed on the thin-film insulator layer formed by the step of forming a microbridge structure, a PtW film having a thickness of 0.2 μm was formed on the Cr film and a Cr film having a thickness of 0.035 μm was further formed on the PtW film. In this manner, a Cr/PtW/Cr multi-layer film having a thickness of 0.27 μm was formed on the thin-film insulator layer. The Cr film and the PtW film were formed by the sputtering technique.

Subsequently, patterning was performed on the multi-layer film by the photolithography technique and the multi-layer film was etched to form a heater layer.

<Step of Forming Gas Detection Layer>

After an $SiO_2$ film (second insulating film) having a thickness of 2 to 4 μm was formed on the heater layer formed by the step of forming a heater layer, a Cr film having a thickness of 0.035 μm was formed on the $SiO_2$ film and a PtW film having a thickness of 0.2 μm was further formed thereon. The $SiO_2$ film, the Cr film and the PtW film were formed by the sputtering technique.

Subsequently, after patterning was performed on the PtW film by the photolithography technique, the PtW film was etched to form a thermistor electrode part.

Thereafter, a thin film comprising an $Fe_2O_3$—$TiO_2$—MgO composite metal oxide ($Fe_2O_3$/$TiO_2$ (5 mol %)/MgO (4 mol %)) was deposited by a liftoff technique and the sputtering technique over a region in which comb-shaped electrodes (comb tooth portion) were formed in the thermistor electrode part to form a thin-film thermistor part. In this manner, a gas detection layer was formed.

<Step of Producing Catalyst Layer>

After an $SiO_2$ film (third insulating film) having a thickness of 2 to 4 μm was formed on the gas detection layer by the sputtering technique, a mixture of $SnO_2$ nanoparticles, a PVA solution and a Pa colloid solution was placed on the $SiO_2$ film and subjected to a thermal treatment (baking). In this manner, a catalyst layer comprising Pd/$SnO_2$ was produced so as to be positioned above the thin-film thermistor part.

The thus produced contact combustion type gas sensor was operated under conditions to achieve an operating temperature of 150° C., and responsiveness of the contact combustion type gas sensor when a hydrogen gas at a concentration of 10,000 ppm was supplied to the contact combustion type gas sensor was studied. The result is shown in FIG. 7.

Figure 7:
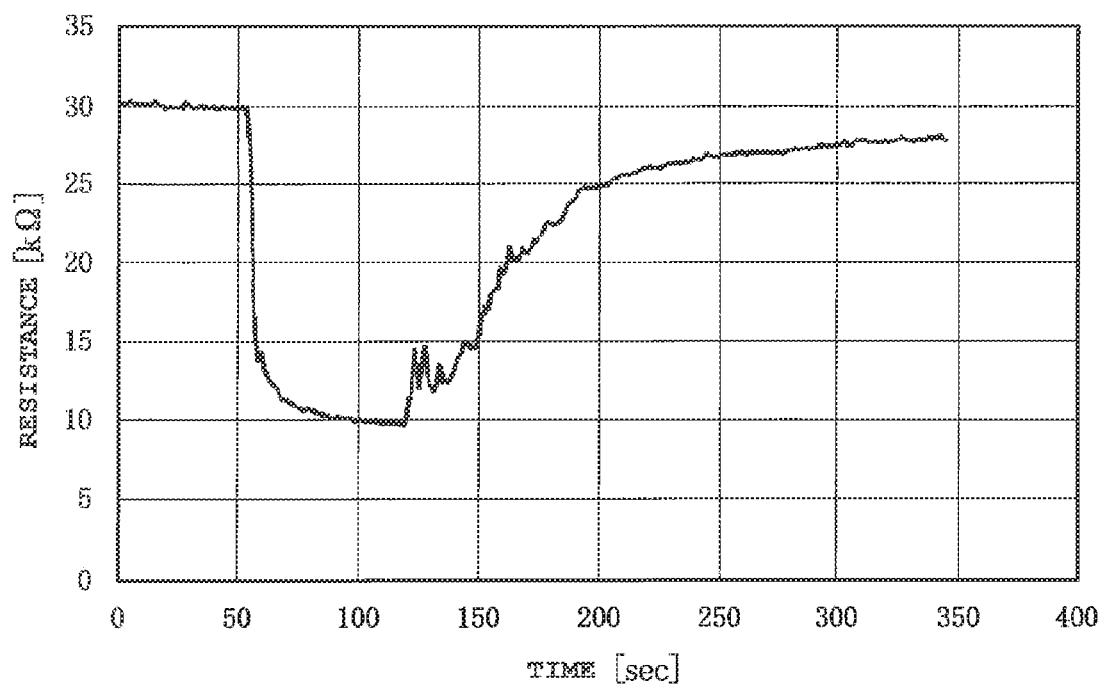
[FIG. 7] is a graph showing responsiveness to a hydrogen gas in a contact combustion type gas sensor produced in Example 1.

The result of FIG. 7 shows that the contact of the hydrogen gas reduced the resistance value of the thin-film thermistor part to magnitude about. ⅓ of the magnitude before the supply of the hydrogen gas. Thus, it was confirmed that the rate of change in resistance value with respect to a temperature change is high. Moreover, the response time was about 23 seconds, and the recovery time was about 1.10 seconds. Thus, it was confirmed that high responsiveness to the gas can be obtained.

While the embodiment of the present invention has been described above with reference to the contact combustion type gas sensor, various modifications can be made thereto in the present invention. For example, the gas sensor of the present invention is not limited to the gas sensor having the microbridge structure, but may have a diaphragm structure in which a thin-film insulator layer is provided so as to cover the entire opening of a cavity portion in a substrate, for example. In the gas sensor having such a configuration, a gas detection element is supported on a diaphragm part positioned on the cavity portion of the substrate in a first insulating film provided on a surface of the substrate.

Figure 8:
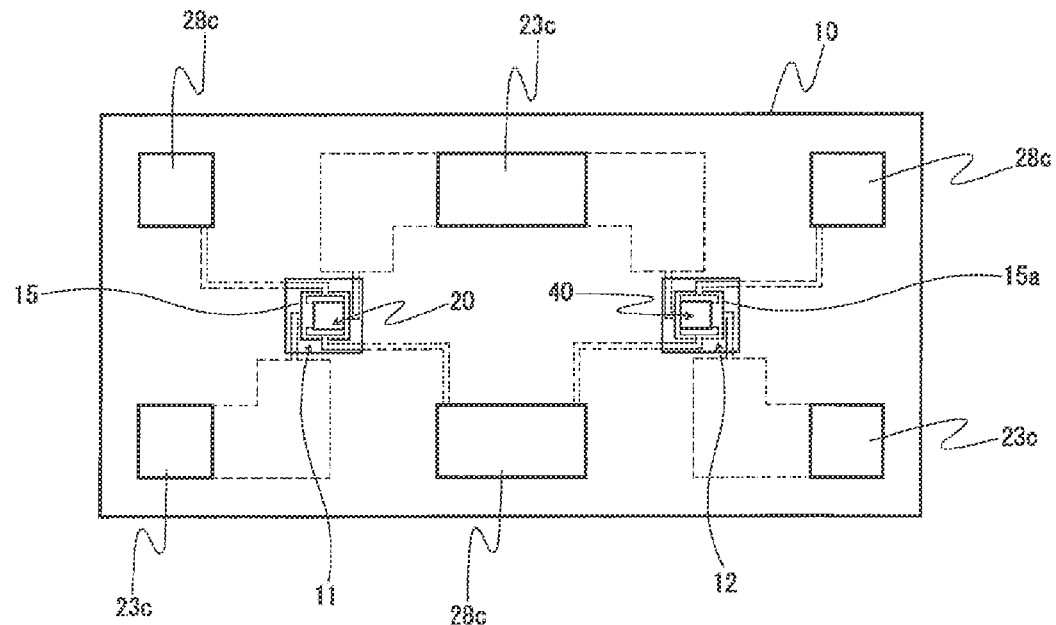
[FIG. 8] is a plan view schematically illustrating another configuration example of the contact combustion type gas sensor according to the present invention.

The gas sensor of the present invention may be configured to include a temperature compensation element as mentioned above. In the gas sensor having such a configuration, a temperature compensation element 40 is disposed on a thin-film insulator layer 15a provided on a cavity portion 12 provided at a position spaced apart from the cavity portion 11 related to the gas detection element 20 as shown in FIG. 8. The temperature compensation element 40 has the same configuration as the gas detection element 20 except that no catalyst is included or a catalyst different from the catalyst of the gas detection element 20 is used.

Without being limited to the contact combustion type gas sensor, the present invention can be configured as a heat conduction type gas sensor that detects a temperature change due to heat conduction of a gas being in contact with a gas detection element.

REFERENCE SIGNS LIST 10 substrate
11 cavity portion
11a opening edge
12 cavity portion
15 thin-film insulator layer
15a thin-film insulator layer
16 first insulating film
17 base part
18a support beam
18b support beam
20 gas detection element
21 heater layer
22 thin-film heater
23a neat generation part
23b lead part
23c heater electrode part
24 second insulating film
25 gas detection layer
26 thin-film thermistor part
27 thermistor electrode part
28a comb-shaped electrode
28b lead part
28c terminal part
29 third insulating film
30 catalyst layer
40 temperature compensation element

The invention claimed is:

1. A gas sensor comprising:
a substrate comprising a semiconductor substrate and a cavity portion;
a thin-film insulator layer disposed on the cavity portion; and
a gas detection element disposed on the thin-film insulator layer, the gas detection element including:
a heater layer provided on the thin-film insulator layer; and
a gas detection layer having a thin-film thermistor part and an electrode part in contact with the thin-film thermistor part, the gas detection layer being provided on the heater layer so as to be electrically insulated from the heater layer, the thin-film thermistor part comprising a negative characteristic thermistor comprising an $Fe_2O_3$—$TiO_2$—MgO composite metal oxide;
wherein
the gas sensor is adapted to use a MEMS method; and
the gas sensor detects a temperature change due to contact of a gas with the gas detection element on a basis of a change in resistance value in the thin-film thermistor part.

2. The gas sensor according to claim 1, wherein the gas detection element includes a catalyst layer provided on the thin-film thermistor part in the gas detection layer, so that the gas sensor detects a temperature change due to combustion heat of the catalyst layer on a basis of a change in resistance value in the thin-film thermistor part.

3. The gas sensor according to claim 1, wherein in the composite metal oxide, a ratio of $TiO_2$ relative to $Fe_2O_3$ is 0.1 to 10 mol %, and a ratio of MgO relative to $Fe_2O_3$ is 0.5 to 10 mol %.

4. The gas sensor according to claim 1, comprising a second cavity portion provided at a position spaced apart from the cavity portion related to the gas detection element, a second thin-film insulator layer provided on the second cavity portion, and a compensation element disposed on the second thin-film insulator layer.

* * * * *